United States Patent
Shimada (10) Patent No.: US 10,709,614 B2
(45) Date of Patent: *Jul. 14, 2020

(54) DISPOSABLE DIAPER PRODUCTION METHOD

(71) Applicant: ZUIKO CORPORATION, Settsu-shi, Osaka (JP)

(72) Inventor: Takahiro Shimada, Osaka (JP)

(73) Assignee: Zuiko Corporation (JP)

( * ) Notice: Subject to any disclaimer, the term of this patent is extended or adjusted under 35 U.S.C. 154(b) by 1070 days.

This patent is subject to a terminal disclaimer.

(21) Appl. No.: 14/649,083

(22) PCT Filed: Dec. 19, 2013

(86) PCT No.: PCT/JP2013/007470
§ 371 (c)(1),
(2) Date: Jun. 2, 2015

(87) PCT Pub. No.: WO2014/097635
PCT Pub. Date: Jun. 26, 2014

(65) Prior Publication Data
US 2016/0213523 A1    Jul. 28, 2016

(30) Foreign Application Priority Data
Dec. 21, 2012   (JP) ................. 2012-280109

(51) Int. Cl.
*A61F 13/15* (2006.01)
*A61F 13/496* (2006.01)

(52) U.S. Cl.
CPC .. *A61F 13/15585* (2013.01); *A61F 13/15739* (2013.01); *A61F 13/15747* (2013.01);
(Continued)

(58) Field of Classification Search
CPC . A61F 13/4963; A61F 13/15739; B26D 7/18; B26D 7/1836
See application file for complete search history.

(56) References Cited

U.S. PATENT DOCUMENTS 5,246,433 A    9/1993 Hasse et al.
5,464,401 A    11/1995 Hasse et al.
(Continued)

FOREIGN PATENT DOCUMENTS

CN    1717313 A    1/2006
EP    0320989 A2 *  6/1989    ....... A61F 13/15593
(Continued)

OTHER PUBLICATIONS

European Search Report dated May 25, 2016.
Chinese Office Action and Translation dated Nov. 28, 2016.

*Primary Examiner* — Barbara J Musser
(74) *Attorney, Agent, or Firm* — Gerald E. Hespos; Michael J. Porco; Matthew T. Hespos (57) ABSTRACT

A welding unit welds respective side panels pieces of a partly-finished product being conveyed by a conveying unit to each other along a conveying direction. The conveying unit conveys, when the respective side panel pieces are welded to each other by the welding unit, the partly-finished product in a state in which both side portions in the width direction of the portions of the respective side panel pieces to be welded are held for each set of the respective side panel pieces.

4 Claims, 8 Drawing Sheets

(52) U.S. Cl.
CPC .. *A61F 13/15756* (2013.01); *A61F 13/15764* (2013.01); *A61F 13/496* (2013.01); *A61F 2013/15869* (2013.01)

(56) References Cited

U.S. PATENT DOCUMENTS

| | | | | |
|---|---|---|---|---|
| 5,496,429 | A | | 3/1996 | Hasse et al. |
| 5,616,201 | A | * | 4/1997 | Finch ...................... A47K 7/02 156/204 |
| 5,626,711 | A | * | 5/1997 | Herrmann ......... A61F 13/15577 156/163 |
| 5,683,531 | A | * | 11/1997 | Roessler ........... A61F 13/15593 156/163 |
| 5,700,340 | A | * | 12/1997 | Johnson ............. A44B 18/0069 156/152 |
| 5,735,991 | A | * | 4/1998 | Strongwater ........... B29C 65/04 156/239 |
| 5,772,825 | A | * | 6/1998 | Schmitz ............ A61F 13/15747 156/163 |
| 6,253,819 | B1 | * | 7/2001 | Frendle .................. B26D 3/085 156/518 |
| 8,292,792 | B2 | * | 10/2012 | Yamamoto ........ A61F 13/15699 493/343 |
| 8,925,607 | B2 | * | 1/2015 | Yamamoto ........ A61F 13/15739 156/359 |
| 9,808,379 | B2 | * | 11/2017 | Hamamoto ......... A61F 13/4963 |
| 2003/0015296 | A1 | * | 1/2003 | Pelagatti .............. B65H 19/105 156/504 |
| 2003/0120252 | A1 | * | 6/2003 | Franke .................. A61F 13/496 604/392 |
| 2004/0118505 | A1 | * | 6/2004 | Shimakawa ...... A61F 13/15593 156/164 |
| 2005/0092146 | A1 | * | 5/2005 | Carbone, II ............. B26D 7/18 83/13 |
| 2005/0145317 | A1 | | 7/2005 | Yamamoto |
| 2006/0065354 | A1 | * | 3/2006 | Mischler ........... A61F 13/15682 156/216 |
| 2007/0095463 | A1 | * | 5/2007 | Frendle .................. B26D 7/088 156/250 |
| 2007/0251364 | A1 | * | 11/2007 | Blumle .................. B26D 7/018 83/100 |
| 2008/0083489 | A1 | * | 4/2008 | Schneider ......... A61F 13/15739 156/258 |
| 2011/0040273 | A1 | * | 2/2011 | Sablone ............ A61F 13/15593 604/378 |
| 2011/0125122 | A1 | * | 5/2011 | Thorson ............ A61F 13/15593 604/385.3 |
| 2012/0055615 | A1 | * | 3/2012 | Back ................. A61F 13/15609 156/177 |
| 2012/0079926 | A1 | * | 4/2012 | Long ................. A61F 13/15707 83/27 |
| 2012/0178609 | A1 | * | 7/2012 | Yamamoto ........ A61F 13/15747 493/454 |
| 2012/0211538 | A1 | * | 8/2012 | Yamamoto ........ A61F 13/15764 226/95 |
| 2012/0247681 | A1 | * | 10/2012 | Yamamoto ........ A61F 13/15609 156/510 |
| 2012/0302417 | A1 | * | 11/2012 | Gouda ............. A61F 13/15593 493/346 |
| 2013/0075038 | A1 | * | 3/2013 | McCabe ............. B32B 37/0053 156/349 |
| 2013/0160194 | A1 | | 6/2013 | Shimada |
| 2013/0283987 | A1 | * | 10/2013 | Pras .......................... B26D 7/22 83/344 |
| 2015/0250655 | A1 | * | 9/2015 | Kawka .............. A61F 13/15764 156/64 |

FOREIGN PATENT DOCUMENTS

| | | |
|---|---|---|
| EP | 1609582 A1 | 12/2005 |
| JP | 3-126529 | 5/1991 |
| JP | 7-501245 | 2/1995 |
| JP | 3386124 | 1/2003 |
| JP | 2005-521475 | 7/2005 |
| JP | 2006007639 A | 1/2006 |
| WO | 2012032732 A1 | 3/2012 |

* cited by examiner

DISPOSABLE DIAPER PRODUCTION METHOD

TECHNICAL FIELD

The present invention relates to a disposable diaper production method and a disposable diaper production device for producing a disposable diaper having a main body portion that extends from a front belly part to a back part via a crotch part and a pair of side portions that covers the side surfaces of the lumbar part of a wearer when the disposable diaper is worn.

BACKGROUND ART

Conventionally, disposable toilet-training underpants described in, for example, Japanese Patent No. 3386124 have been known as such. The training underpants have a portion (hereinafter referred to as a main body portion) that extends from a front belly part to a back part via a crotch part and four side surface portions (hereinafter referred to as side pieces) that extend from both ends in the longitudinal direction of the main body portion in their width direction.

The training underpants described in Japanese Patent No. 3386124 have a pair of portions (hereinafter referred to as side portions) that covers the side surfaces of the lumbar part of a wearer, the pair of portions being formed when the respective side pieces are welded to each other by ultrasonic welding in a state that the main body portion is folded in two so that the side pieces overlap each other.

Here, Japanese Patent No. 3386124 also discloses an ultrasonic device that forms the side portions. The ultrasonic device has an anvil and an ultrasonic horn that compresses the respective side pieces between the ultrasonic horn and the anvil to weld the respective side pieces to each other by ultrasonic welding.

However, the ultrasonic device described in Japanese Patent No. 3386124 welds the respective side pieces to each other only by the anvil and the ultrasonic horn. Therefore, the welding positions of the respective side pieces cannot be accurately managed.

That is, in the ultrasonic device described in Japanese Patent No. 3386124, the respective side pieces are freely movable with respect to the ultrasonic device until the respective side pieces are compressed between the anvil and the ultrasonic horn. Therefore, the welding positions fluctuate in accordance with the positions of the respective side pieces.

SUMMARY OF INVENTION

It is an object of the present invention to provide a disposable diaper production method and a disposable diaper production device by which the welding positions of respective side pieces can be accurately managed.

In order to solve the problem, the present invention provides a disposable diaper production method for producing a disposable diaper having a main body portion that extends from a front belly part to a back part via a crotch part and a pair of side portions that covers side surfaces of a lumbar part of a wearer when the disposable diaper is worn, the method including: a constituents producing step of producing constituents including the main body portion and four side pieces each of which protrudes from both ends of the main body portion in a longitudinal direction to both outer sides in a width direction of the main body portion; a folding step of folding the main body portion in the longitudinal direction to form two sets of two mutually-overlapping side pieces; a conveying step of conveying the folded constituents along the longitudinal direction; and a welding step of welding the mutually-overlapping side pieces to each other along a conveying direction for each set of the two side pieces of the constituents being conveyed to form the pair of side portions, wherein the conveying step conveys the constituents in a state in which both side portions in the width direction of a portion of the respective side pieces to be welded are held for each set of the two side pieces when the respective side pieces are welded to each other in the welding step.

In addition, the present invention provides a disposable diaper production device for producing a disposable diaper having a main body portion that extends from a front belly part to a back part via a crotch part and a pair of side portions that covers side surfaces of a lumbar part of a wearer when the disposable diaper is worn, the device including: a folding unit that folds the main body portion in a longitudinal direction to form two sets of two mutually-overlapping side pieces for constituents including the main body portion and four side pieces each of which protrudes from both ends of the main body portion in the longitudinal direction to both outer sides in a width direction of the main body portion; a conveying unit that conveys the folded constituents along the longitudinal direction; and a welding unit that welds the mutually-overlapping side pieces to each other along a conveying direction for each set of the two side pieces of the constituents being conveyed to form the pair of side portions, wherein the conveying unit conveys the constituents in a state in which both side portions in the width direction of a portion of the respective side pieces to be welded are held for each set of the two side pieces when the respective side pieces are welded to each other by the welding unit.

According to the present invention, the welding positions of respective side pieces can be accurately managed.

DESCRIPTION OF EMBODIMENTS

Hereinafter, a description will be given of an embodiment of the present invention with reference to the accompanying drawings. Note that the following embodiment is a materialized example of the present invention but does not limit the technical scope of the present invention.

Figure 1:
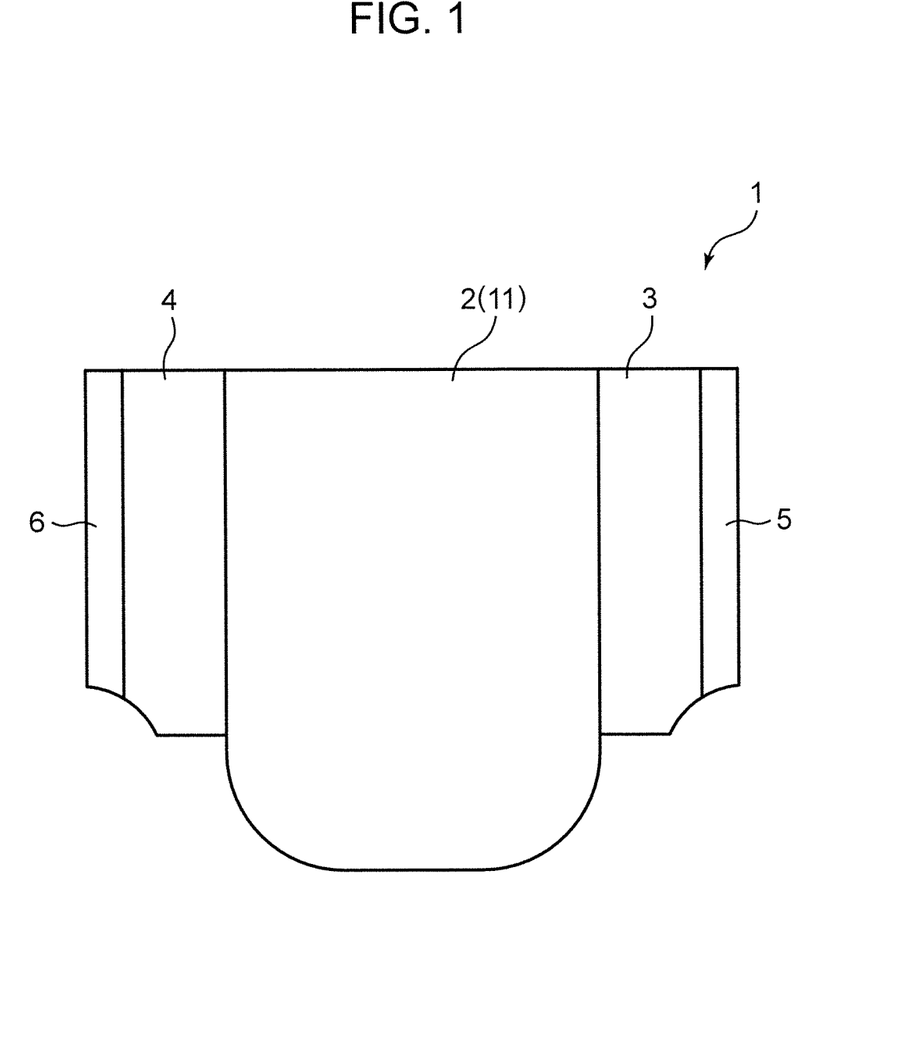
FIG. 1 is a front view showing a disposable diaper according to an embodiment of the present invention.
Figure 2:
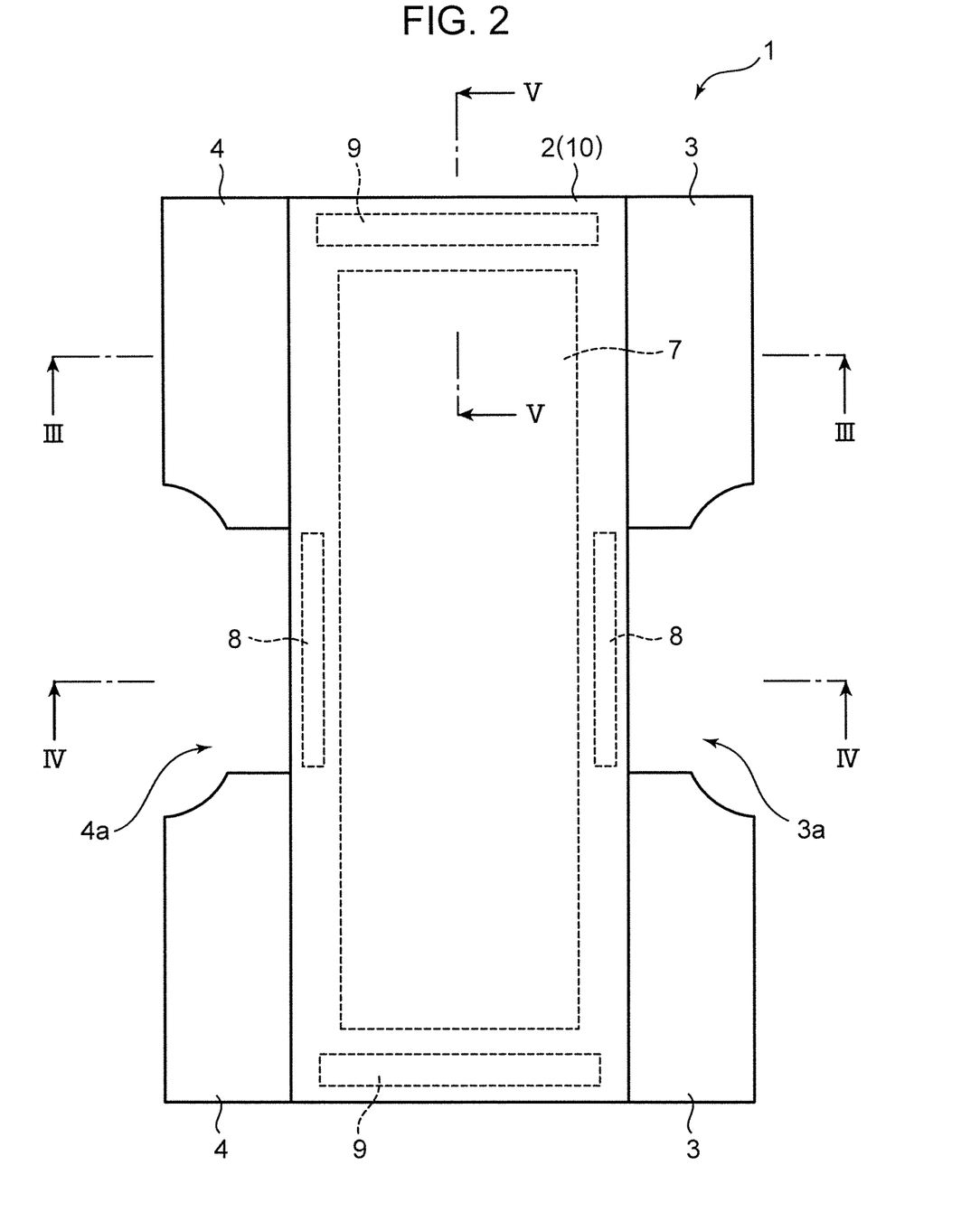
FIG. 2 is a plan view showing the disposable diaper shown in FIG. 1 in a state that the side seal portions are unfolded.

With reference to FIGS. 1 and 2, a disposable diaper 1 as an example of disposable wearing articles is a so-called underpants-shaped diaper. Specifically, a disposable diaper 1 has a diaper main body (main body portion) 2 that extends from the front belly part to the back part via the crotch part of a wearer and four side panel pieces (side pieces) 3 and 4 each of which protrudes from both ends in the longitudinal direction (vertical direction in FIG. 2) of the diaper main body 2 in the width direction (horizontal direction in FIG. 2) of the diaper main body 2 when the disposable diaper 1 is worn. The disposable diaper 1 is formed in an underpants shape when the respective side panel pieces 3 are bonded to each other through their side seal portions 5 and the respective side panel pieces 4 are bonded to each other through their side seal portions 6 in a state in which the diaper main body 2 is folded in two. As a result, the respective side panel pieces 3 bonded to each other through the side seal portions 5 and the respective side panel pieces 4 bonded to each other through the side seal portions 6 constitute a pair of side portions that covers the side surfaces of the lumbar part of a wearer.

Hereinafter, a description will be given of the specific configuration of the disposable diaper 1 with reference to FIGS. 1 to 5.

The diaper main body 2 is capable of absorbing body wastes (for example, urine) of a wearer and has elasticity at its appropriate portions. Specifically, the diaper main body 2 has an absorber 7 capable of absorbing body wastes of a wearer, elastic members 8 for legs provided at positions corresponding to the crotch part of the wearer, a pair of elastic members 9 for waist provided at positions corresponding to the front belly part and the back part of the wearer, and inner and outer sheets 10 and 11 that sandwich the absorber 7, the elastic members 8 for legs, and the elastic members 9 for waist between them.

The inner sheet 10 is a substantially rectangular sheet that is directed to the body surface side of a wearer when the disposable diaper 1 is worn and has liquid permeability. The inner sheet 10 can be constituted by, for example, a nonwoven sheet and/or a mesh sheet having liquid permeability.

The outer sheet 11 is a sheet that is directed to the outer side of a wearer when the disposable diaper 1 is worn and has liquid impermeability. The outer sheet 11 can be constituted by a polyethylene film or a nonwoven fabric having water repellency and air permeability. In addition, the outer sheet 11 is a substantially rectangular sheet having a size equivalent to that of the inner sheet 10.

Figure 3:
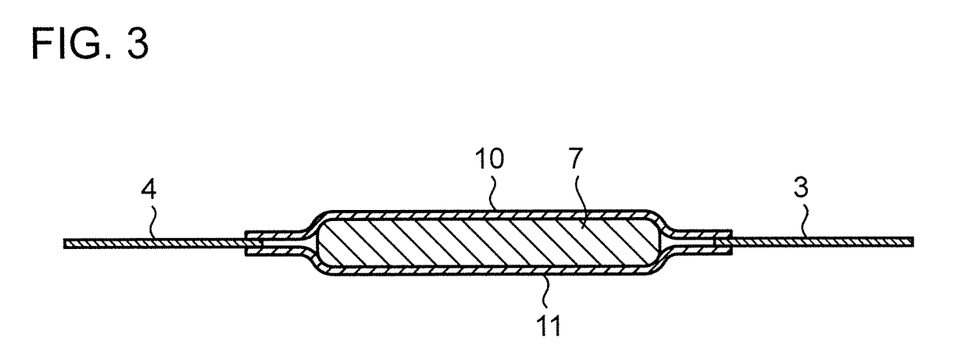
FIG. 3 is a cross-sectional view taken along line III-III in FIG. 2.

The absorber 7 absorbs liquid that passes through the inner sheet 10. Specifically, the absorber 7 is molded in such a way as to stack crashed pulps or materials in which crashed pulps and highly water-absorptive polymers are mixed together. In addition, the absorber 7 has a substantially rectangular shape or a hourglass shape having a longitudinal size smaller than those of the respective sheets 10 and 11 and a width size narrower than those of the respective sheets 10 and 11. The absorber 7 is arranged between the sheets 10 and 11 such that vacant areas exist at both end portions in the longitudinal direction of the respective sheets 10 and 11 and at both end portions in the width direction (horizontal direction) of the respective sheets 10 and 11. Further, as shown in FIG. 3, the absorber 7 is bonded to the sheets 10 and 11 in a state of being sandwiched between the inner sheet 10 and the outer sheet 11.

Figure 4:
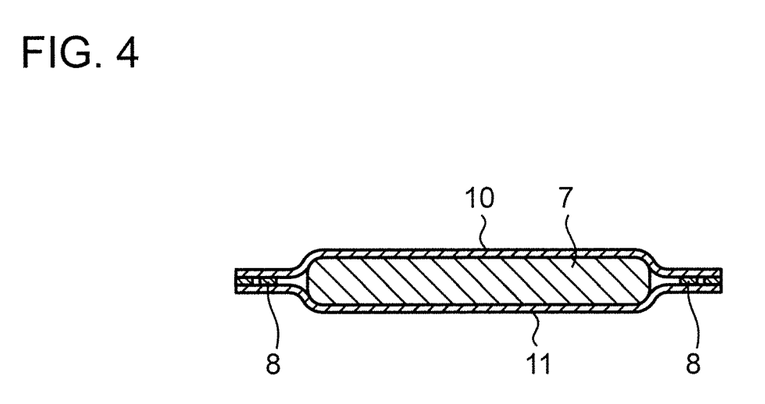
FIG. 4 is a cross-sectional view taken along line IV-IV in FIG. 2.

The respective elastic members 8 for legs are such that the diaper main body 2 is raised and brought into intimate contact with the crotch part of a wearer when the disposable diaper 1 is worn to prevent body wastes from leaking from the gap between the diaper main body 2 and the body surface of the wearer. At least parts of the respective elastic members 8 for legs are provided at positions on both outer sides in the width direction of the absorber 7 and at positions between the respective side panel pieces 3 and between the respective side panel pieces 4. In addition, the respective elastic members 8 for legs are attached on the diaper main body 2 in their expanding state in the longitudinal direction of the diaper main body 2. As shown in FIG. 4, the respective elastic members 8 for legs are bonded to the sheets 10 and 11 in a state of being sandwiched between the inner sheet 10 and the outer sheet 11. The respective elastic members 8 for legs can be constituted by polyurethane, natural rubber, or sheets or threads made of a thermoplastic resin.

Figure 5:
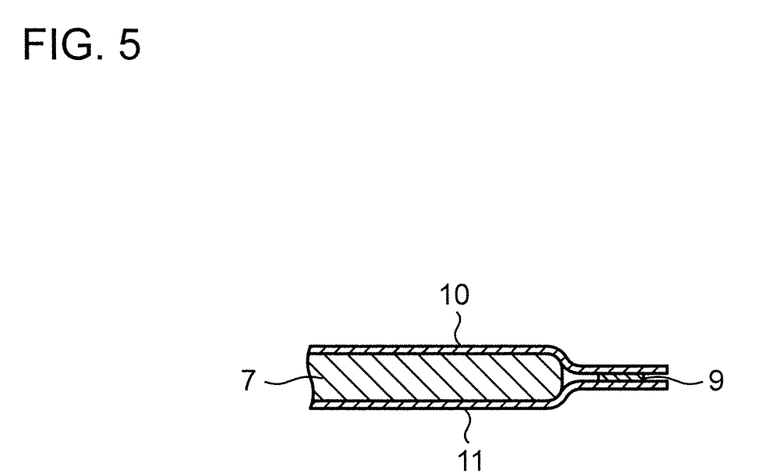
FIG. 5 is a cross-sectional view taken along line V-V in FIG. 2.

The respective elastic members 9 for waist are such that the diaper main body 2 is fastened to the front belly part or the back part of a wearer when the disposable diaper 1 is worn to prevent the disposable diaper 1 from being pulled down. The respective elastic members 9 for waist are attached on the diaper main body 2 under a stretched state in the width direction of the absorber 7. As shown in FIG. 5, the respective elastic members 9 for waist are bonded to the sheets 10 and 11 in a state of being sandwiched between the inner sheet 10 and the outer sheet 11. The respective elastic members 9 for waist can be constituted by polyurethane, natural rubber, or sheets or threads made of a thermoplastic resin.

The respective side panel pieces 3 extend from both end portions in the longitudinal direction (front and rear direction) of the diaper main body 2 to one side in the horizontal direction (right side in FIGS. 1 and 2) and has elasticity in the horizontal direction. A gap portion 3a is formed between the respective side panel pieces 3 and used as a leg hole when the right edge portions of the respective side panel pieces 3 are bonded to each other through the side seal portions 5. As shown in FIG. 3, the respective side panel pieces 3 are bonded to the sheets 10 and 11 in a state of being sandwiched between the inner sheet 10 and the outer sheet 11 on the right side of the absorber 7.

In addition, the respective side panel pieces 3 are sheets made of a thermoplastic material. Specifically, the respective side panel pieces 3 can be constituted by an elastic film, an elastic nonwoven fabric, a laminated body of an elastic film and a nonwoven fabric, or a laminated body of thread rubber and a nonwoven fabric each of which is made of one or at least two of the materials of a block copolymer of polystyrene, a block copolymer of polyisoprene, a block copolymer of polybutadiene, a copolymer of ethylene, natural rubber, and urethane.

The respective side panel pieces 4 extend from both end portions in the longitudinal direction of the diaper main body 2 to one side in the horizontal direction (left side in FIGS. 1 and 2) and has elasticity in the horizontal direction. A gap portion 4a is formed between the respective side panel pieces 4 and used as a leg hole when the left edge portions of the respective side panel pieces 4 are bonded to each other through the side seal portions 6. As shown in FIG. 3, the respective side panel pieces 4 are bonded to the sheets 10 and 11 in a state of being sandwiched between the inner sheet 10 and the outer sheet 11 on the left side of the absorber 7.

In addition, the respective side panel pieces 4 are sheets made of a thermoplastic material. Specifically, the respective side panel pieces 4 can be constituted by an elastic film, an elastic nonwoven fabric, a laminated body of an elastic film and a nonwoven fabric, or a laminated body of thread rubber and a nonwoven fabric each of which is made of one or at least two of the materials of a block copolymer of polystyrene, a block copolymer of polyisoprene, a block copolymer of polybutadiene, a copolymer of ethylene, natural rubber, and urethane.

Hereinafter, a description will be given of a method of producing the disposable diaper 1 with reference to FIG. 6. The method of producing the disposable diaper 1 mainly includes the following steps S1 to S13.

<Step S1>

In step S1, an outer sheet band 11A for constituting the outer sheet 11 is continuously conveyed in its longitudinal direction.

<Step S2>

In step S2, the elastic members 9 for waist are bonded to the continuously-conveyed outer sheet band 11A. Specifically, the elastic members 9 for waist are arranged at two parts on the outer sheet band 11A with an interval corresponding to the longitudinal size of the absorber 7. In addition, the elastic members 9 for waist at the two parts attached in step S2 are separated from each other in the longitudinal direction (flow direction) of the outer sheet band 11A. Moreover, the respective elastic members 9 for waist are attached on the outer sheet band 11A under a stretched state in the width direction of the outer sheet band 11A.

<Step S3>

In step S3, the absorber 7 is bonded to the continuously-conveyed outer sheet band 11A. Specifically, the absorber 7 is arranged between the respective elastic members 9 for waist in a state that a longitudinal direction of the absorber 7 is disposed along the longitudinal direction of the outer sheet band 11A.

<Step S4>

In step S4, the pair of elastic members 8 for legs is bonded to the continuously-conveyed outer sheet band 11A. The elastic members 8 for legs are arranged at a central position in the longitudinal direction of the absorber 7 on the outer sheet band 11A and at positions on both outer sides in the width direction of the absorber 7. In addition, the respective elastic members 8 for legs are attached on the outer sheet band 11A under a stretched state in the longitudinal direction of the outer sheet band 11A.

<Step S5>

In step S5, a side panel band 3A for constituting the side panel pieces 3 and a side panel band 4A for constituting the side panel pieces 4 are bonded to the continuously-conveyed outer sheet band 11A. The side panel bands 3A and 4A are continuously supplied in a state that longitudinal directions of the side panel bands 3A and 4A are disposed along the longitudinal direction of the outer sheet band 11A and bonded to the edge portions of the outer sheet band 11A on the outer side of the elastic members 8 for legs. At this time, the side panel bands 3A and 4A are bonded to the outer sheet band 11A in a state of protruding from the outer sheet band 11A.

<Step S6>

In step S6, an inner sheet band 10A for constituting the inner sheet 10 is bonded to the continuously-conveyed outer sheet band 11A. Specifically, the inner sheet band 10A is continuously supplied in a state that a longitudinal direction of the inner sheet band 10A is disposed along the longitudinal direction of the outer sheet band 11A and bonded to the outer sheet band 11A in a state of being aligned with the outer sheet band 11A in the width direction. In step S6, the respective elastic members 8 and 9 and the absorber 7 are entirely sandwiched between the sheet bands 10A and 11A, and the edge portions of the side panel bands 3A and 4A are sandwiched between the sheet bands 10A and 11A.

<Step S7>

In step S7, the side panel bands 3A and 4A are cut off to form the gap portions 3a and 4a. At this time, the side panel bands 3A and 4A are cut off over a predetermined range in the longitudinal direction of the respective side panel bands 3A and 4A, including the central position in the longitudinal direction of the absorber 7.

<Step S8>

In step S8, the sheet bands 10A and 11A and the side panel bands 3A and 4A are cut off to form a partly-finished product (constituent) 1Z of a disposable diaper. Specifically, the sheet bands 10A and 11A and the side panel bands 3A and 4A are cut off at their positions between the adjacent elastic members 9 for waist. In step S8, the partly-finished product 1Z is formed in which the side panel bands 3A and 4A are separated into the side panel pieces 3 and 4, respectively.

<Step S9>

In step S9, the diaper main body 2 of the partly-finished product 1Z is folded in two at the central position in the longitudinal direction (folding step). Thus, the side panel pieces 3 face each other, and the side panel pieces 4 face each other.

<Step S10>

In step S10, the respective mutually-overlapping side panel pieces 3 and the respective mutually-overlapping side panel pieces 4 are tentatively fastened to each other (tentative fastening step). Specifically, in step S10, tentative fastening portions 3c and 4c are formed at positions corresponding to separated portions 3b and 4b to be separated in step S12 that will be described later. The tentative fastening portions 3c and 4c fasten the respective side panel pieces 3 and the respective side panel pieces 4 to each other to prevent the diaper main body 2 from being unfolded.

<Step S11>

In step S11, the side seal portions 5 are formed on the respective side panel pieces 3, and the side seal portions 6 are formed on the respective side panel pieces 4 (welding step). That is, the respective side panel pieces 3 and the respective side panel pieces 4 are welded to each other by ultrasonic welding.

<Step S12>

In step S12, the separated portion 3b on the outer side of the respective side seal portions 5 of the respective side panel pieces 3 is cut off, and the separated portion 4b on the outer side of the respective side seal portions 6 of the respective side panel pieces 4 is cut off (cutting step). Thus, the edge portions of the respective side panel pieces 3 and the edge portions of the respective side panel pieces 4 are lined up to enhance the appearance. Further, the separated portions 3b and 4b are discarded at a discarding unit 18 that will be described later (discarding step).

<Step S13>

In step S13, the respective side panel pieces 3 and the respective side panel pieces 4 are folded toward the inner side of the diaper main body 2. Thus, the disposable diaper 1 in a form suitable to be packaged is completed.

Hereinafter, a description will be given, with reference to FIGS. 6 and 7, of a disposable diaper production device 14 used in steps S9 to S12 described above.

The production device 14 has a folding unit 15 that executes steps S9 and S10, a welding unit 16 that executes step S11, a cutting unit 17 that executes step S12, the discarding unit 18 that discards the separated portion 4b formed by the cutting unit 17, a conveying unit 19 (see FIG. 11) that conveys the partly-finished product 1Z to respective units 15 to 18 described above, a controller 20 (see FIG. 11) that controls the driving of the respective units 15 to 19, and an input unit 21 (see FIG. 11) used to input a setting value or the like to the controller 20.

Figure 7:
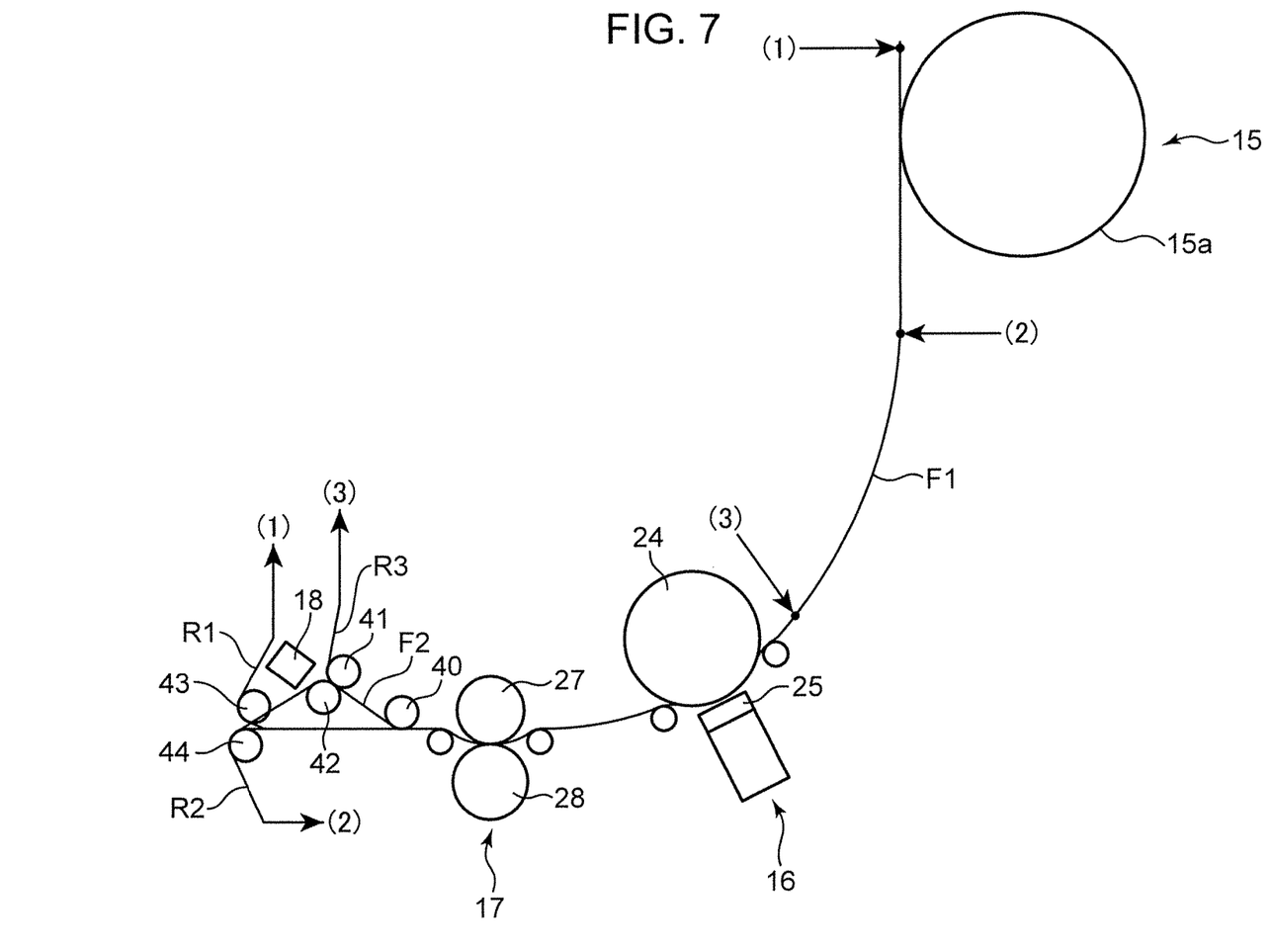
FIG. 7 is a schematic view showing the configuration of a production device used in the production method shown in FIG. 6.
Figure 8:
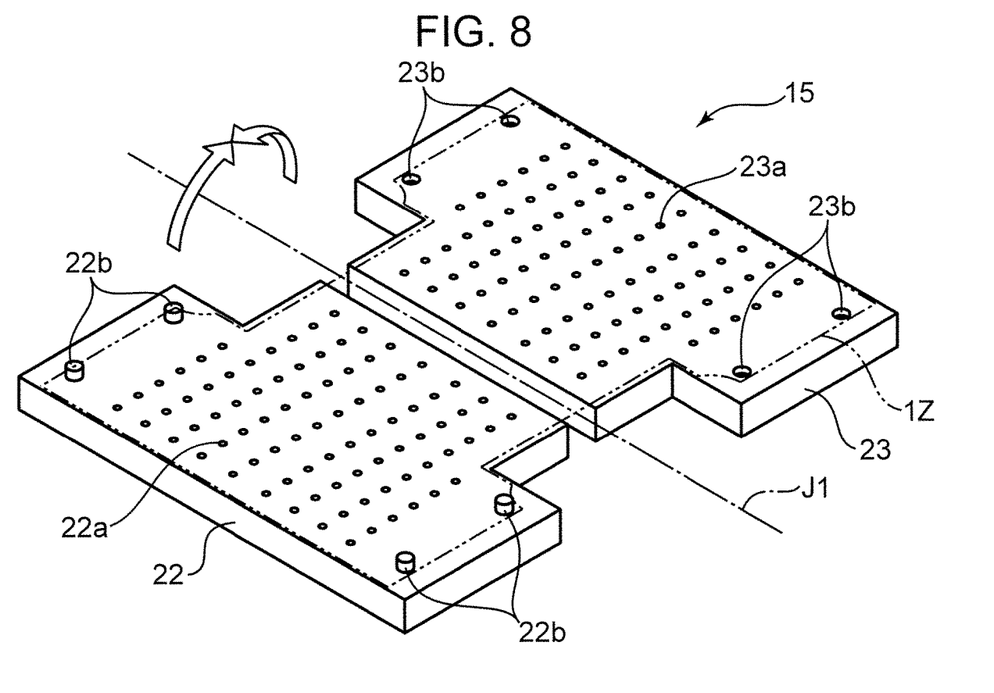
FIG. 8 is a perspective view showing the schematic configuration of a folding unit shown in FIG. 7 in its enlarged state.

With reference to FIGS. 7 and 8, the folding unit 15 has a plurality of sets of first and second holding plates 22 and 23 provided at the periphery of a drum 15a that is rotatable about a predetermined axis and has an opening/closing mechanism (not shown) that opens/closes the respective holding plates 22 and 23 in response to the rotation of the drum 15a. Note that FIG. 8 shows only one set of the holding plates 22 and 23.

The respective holding plates 22 and 23 hold the front half or the rear half of the partly-finished product 1Z by adsorption. Specifically, the respective holding plates 22 and 23, respectively, have suction holes 22a and 23a connected to a suction source (not shown) on their front surface. In addition, the respective holding plates 22 and 23 are rotatable about an axis J1 such that the front half and the rear half of the partly-finished product 1Z held by the respective holding plates 22 and 23 by adsorption come into intimate contact with each other.

Figure 9:
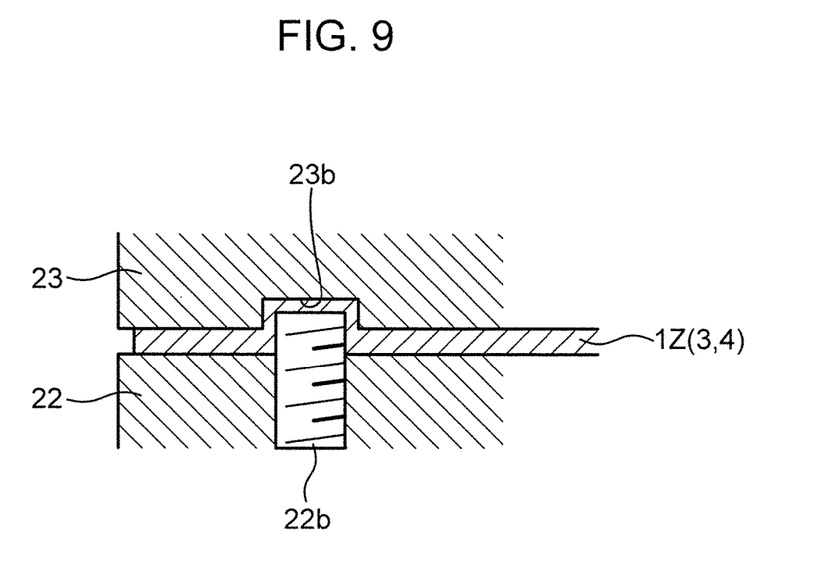
FIG. 9 is a cross-sectional view showing a part of the folding unit shown in FIG. 8.

Moreover, the first holding plate 22 has tentative fastening protruding portions 22b that protrude from its front surface. While, the second holding plate 23 has tentative fastening recessed portions 23b that are capable of receiving the tentative fastening protruding portions 22b at the rotation described above. The tentative fastening protruding portions 22b and the tentative fastening recessed portions 23b are arranged at parts corresponding to the side panel pieces 3 and 4 (the separated portions 3b and 4b) of the partly-finished product 1Z held by adsorption. Therefore, when the respective holding plates 22 and 23 are closed, the side panel pieces 3 and 4 are compressed between the tentative fastening protruding portions 22b and the tentative fastening recessed portions 23b as shown in FIG. 9 to form the tentative fastening portions 3c and 4c. As shown in FIG. 9, the tentative fastening protruding portions 22b are constituted by screw portions. Therefore, the protruding amount of the tentative fastening protruding portions 22b can be adjusted in such a way as to adjust the fastening degree of the tentative fastening protruding portions 22b with respect to the first holding plate 22. Note that although the side panel pieces 3 and 4 are compressed to form the tentative fastening portions 3c and 4c, heat may be applied to the side panel pieces 3 and 4 to form the tentative fastening portions 3c and 4c.

Next, a description will be given of the operation of the folding unit 15.

When the drum 15a rotates to a predetermined receiving position, the respective holding plates 22 and 23 rotate to their opening position as shown in FIG. 8 to receive the unfolded partly-finished product 1Z from an upstream-side line (line in which step S8 is executed). When the drum 15a rotates to the predetermined folding position, the respective holding plates 22 and 23 rotate about the axis J1 to fold the partly-finished product 1Z and form the tentative fastening portions 3c and 4c. Then, when the drum 15a rotates to a predetermined transferring position, the respective holding plates 22 and 23 rotate again to the opening position shown in FIG. 8 to transfer the folded partly-finished product 1Z to the conveying unit 19.

Figure 10:
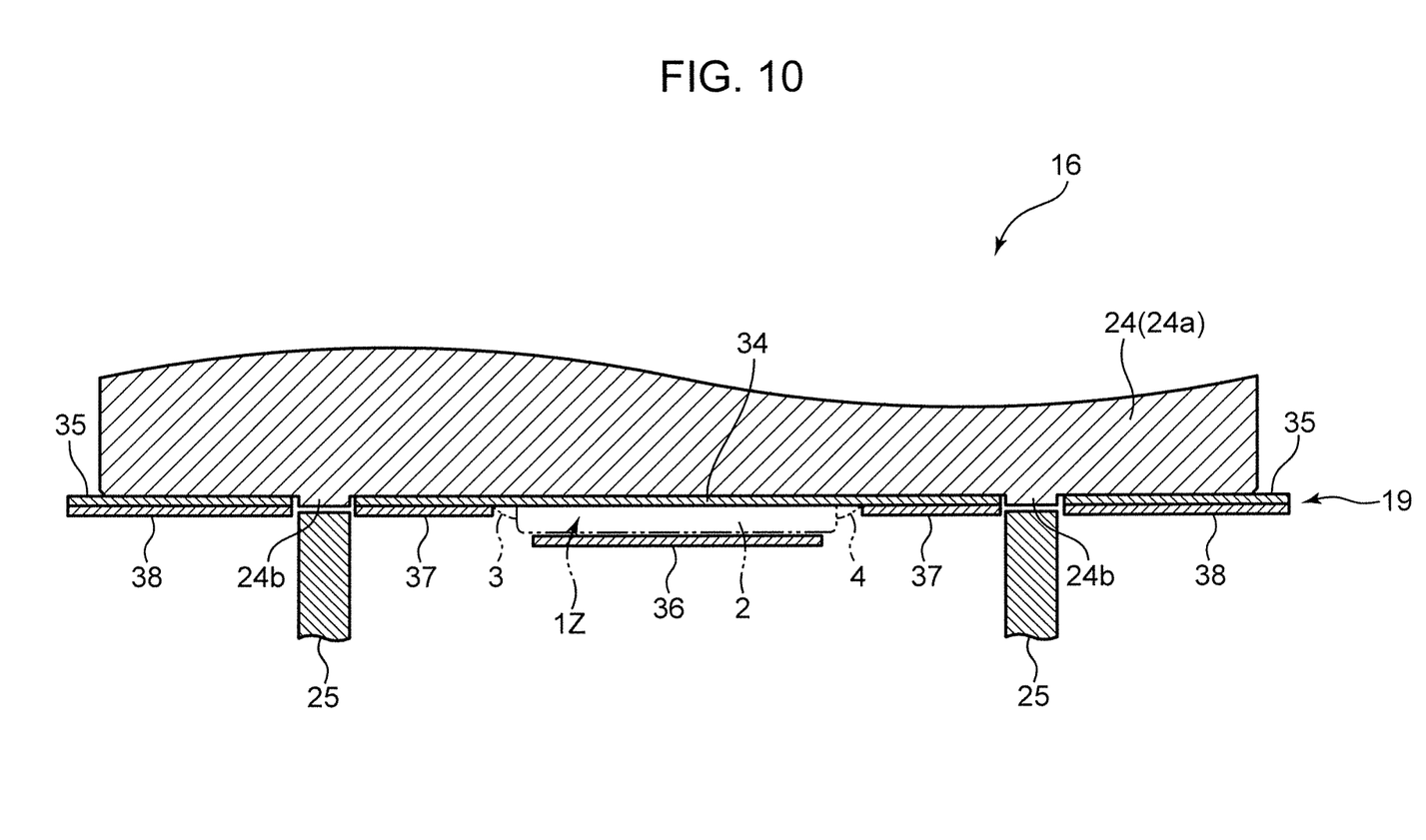
FIG. 10 is a cross-sectional view showing the schematic configuration of a welding unit shown in FIG. 7.

The welding unit 16 forms the side seal portions 5 and 6 on the partly-finished product 1Z being conveyed by the conveying unit 19 that will be described later. Specifically, as shown in FIGS. 7 and 10, the welding unit 16 has an anvil 24 that is rotatable about a predetermined rotating axis and a pair of horns 25 that welds the respective side panel pieces 3 to each other and the respective side panel pieces 4 to each other by ultrasonic welding between the pair of horns 25 and the anvil 24.

The anvil 24 has an anvil main body 24a and a pair of protruding portions 24b that protrudes from the anvil main body 24a to an outside. The respective protruding portions 24b are arranged at an interval corresponding to the pitch between the side seal portions 5 and 6.

Then, the welding unit 16 applies mechanical vibrations from the horns 25 to the respective side panel pieces 3 and 4 while compressing the respective side panel pieces 3 and 4 between the respective protruding portions 24b and the pair of horns 25 to form the side seal portions 5 and 6.

Figure 11:
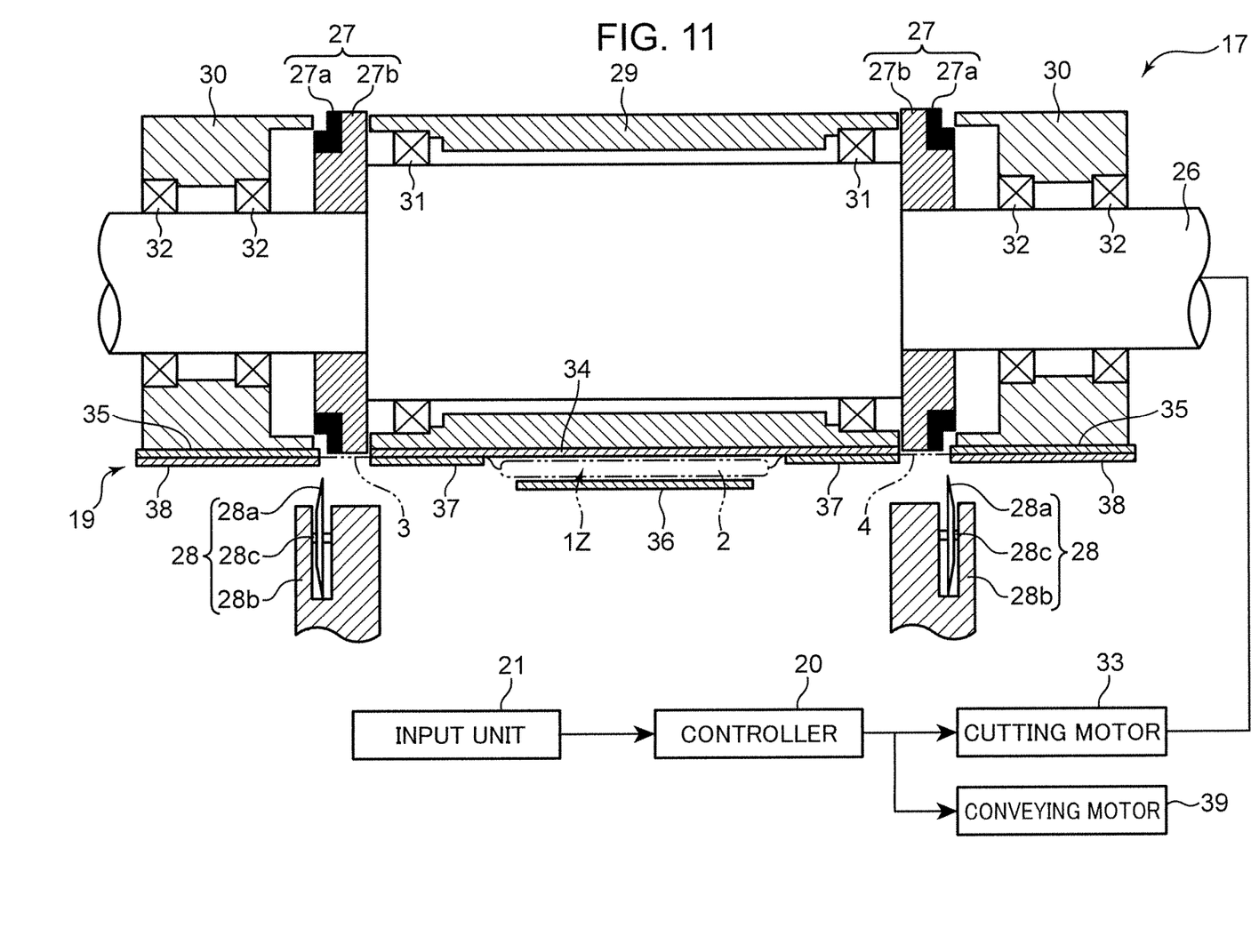
FIG. 11 is a cross-sectional view showing the schematic configuration of a cutting unit shown in FIG. 7 and also shows the electrical configuration relating to the cutting unit.

The cutting unit 17 cuts off the side panel pieces 3 and 4 of the partly-finished product 1Z being conveyed by the conveying unit 19 that will be described later. Specifically, as shown in FIGS. 7 and 11, the cutting unit 17 has a driving shaft 26, a pair of driving blades 27 that rotates and drives in response to the rotation of the driving shaft 26, a pair of driven blades 28 that cuts off the respective side panel pieces 3 and 4 with the driving blades 27, an inner support roller 29 provided at the periphery of the driving shaft 26 between the respective driving blades 27, a pair of outer support rollers 30 provided at the periphery of the driving shaft 26 on the outer sides of the respective driving blades 27, and a cutting motor 33 that drives the driving shaft 26.

The respective driving blades 27 have an attachment portion 27b fixed to the driving shaft 26 and a driving blade main body 27a detachably attached to the attachment portion 27b.

The respective driven blades 28 have a driven blade main body 28a and a support portion 28b that rotatably supports the driven blade main body 28a about rotating shaft 28c. Note that although FIG. 11 shows a state in which the driven blade main bodies 28a separate from the driving blade main bodies 27a downward, the driven blade main bodies 28a and the driving blade main bodies 27a are actually arranged such that the upper potions of the driven blade main bodies 28a and the lower portions of the driving blade main bodies 27a overlap each other when viewed along the axial line of the driving shaft 26. In addition, the driven blade main bodies 28a rotate in response to the movement of the partly-finished product 1Z to be conveyed by the conveying unit 19.

The inner support roller 29 and the respective outer support rollers 30 are used to cause a difference in the rate between a conveying rate for conveying the partly-finished product 1Z by the conveying unit 19 that will be described later and the rotating rate of the respective driving blades 27. Specifically, the inner support roller 29 is attached to the periphery of the driving shaft 26 via bearings 31 on the inner sides of the respective driving blades 27. Similarly, the respective outer support rollers 30 are attached to the periphery of the driving shaft 26 via bearings 32 on the outer sides of the respective driving blades 27.

As shown in FIG. 7, the conveying unit 19 conveys the partly-finished product 1Z along a main path F1 that extends from the folding unit 15 to the next step (rollers 43 and 44 in FIG. 7) via the welding unit 16 and the cutting unit 17. In addition, the conveying unit 19 conveys the separated portions 3b and 4b (see FIG. 6) formed by the cutting unit 17 to the discarding unit 18 along and preferably at an end of a discarding path F2 that branches off from the main path F1 on the downstream side of the cutting unit 17. The discarding unit 18 is used to attract the separated portions 3b and 4b from the conveying unit 19 and guide the separated portion 3b and 4b to a discarding site (not shown).

Hereinafter, a description will be given of the specific configuration of the conveying unit 19 with reference to FIG. 10.

The conveying unit 19 has an inner support belt 34 that supports the partly-finished product 1Z between the respective protruding portions 24b of the anvil 24, a pair of outer support belts (sandwiching member) 35 that supports the partly-finished product 1Z (the side panel pieces 3 and 4) on the outer sides of the respective protruding portions 24b, a main body sandwiching belt 36 that sandwiches the diaper main body 2 between the main body sandwiching belt 36 and the inner support belt 34, a pair of panel sandwiching belts 37 that sandwiches the side panel pieces 3 and 4 between the panel sandwiching belts 37 and the inner support belt 34, a pair of separated portion sandwiching belts (sandwiching members) 38 that sandwiches parts corresponding to the separated portions of the side panel pieces 3 and 4 between the separated portion sandwiching belt 38 and the respective outer support belts 35, a conveying motor 39 (see FIG. 11) that rotates a driving roller (not shown) that drives the respective support belts 34 and 35, and a plurality of rollers 40 to 44 (see FIG. 7) that holds the respective belts 34 to 38.

As shown in FIGS. 10 and 11, the respective support belts 34 and 35 pass through the welding unit 16 and the cutting unit 17 in a state of being pressed to the peripheral surface of the anvil main body 24a of the welding unit 16 and the peripheral surfaces of the support rollers 29 and 30 of the cutting unit 17.

Here, the respective belts 34 to 38 sandwich the partly-finished product 1Z from its front and rear sides on both sides in the width direction of a region of the partly-finished product 1Z, the region including welding positions by the welding unit 16 and cutting positions by the cutting unit 17. Specifically, the inner support belt 34, the main body sandwiching belt 36, and the respective panel sandwiching belts 37 are arranged between the respective protruding portions 24b of the anvil 24 and between the respective cutting blade main bodies 27a. While, the respective outer support belts 35 and the respective separated portion sandwiching belts 38 are arranged on the outer sides of the respective protruding portions 24b and on the outer sides of the respective cutting blade main bodies 27a. Thus, the partly-finished product 1Z can be welded and cut off with its both sides in the width direction of the welding positions and the cutting positions held.

Hereinafter, a description will be given in more detail of the circulating operations of the respective belts 34 to 38 with reference to FIGS. 7, 10, and 11.

The inner support belt 34 moves from a point (1) in the main path F1 shown in FIG. 7 to the transferring position of the folding unit 15 to receive the partly-finished product 1Z. Here, the inner support belt 34 is provided with an adsorption mechanism (not shown), and the partly-finished product 1Z is adsorbed onto the inner support belt 34 by the adsorption force of the adsorption mechanism.

When the respective sandwiching belts 36 to 38 join so as to face the inner support belt 34 at a point (2) in the main path F1, the partly-finished product 1Z is sandwiched between the inner support belt 34 and the respective sandwiching belts 36 and 37.

When the respective outer support belts 35 join so as to face the separated portion sandwiching belts 38 at a point (3) on the upstream side of the welding unit 16 in the main path F1, parts of the partly-finished product 1Z corresponding to the separated portions 3b and 4b are sandwiched between the respective belts 35 and 38.

Then, the respective belts 34 to 38 pass through the welding unit 16 and the cutting unit 17 in this state.

Beginning at the roller 40 on the downstream side of the cutting unit 17, the respective outer support belts 35 and the respective separated portion sandwiching belts 38 move along the discarding path F2 that branches off from the main path F1 along which the other belts 34, 36, and 37 move. Thus, the separated portions 3b and 4b are separated from the other portions of the partly-finished product 1Z or torn off in a case in which the partly-finished product 1Z is imperfectly cut off.

Among the respective belts 34, 36, and 37 that move along the main path F1, the inner support belt 34 returns to the point (1) along a first return path R1 beginning at the roller 43. While, the respective sandwiching belts 36 and 37 return to the point (2) along a second return path R2 beginning at the roller 44. Thus, the partly-finished product 1Z sandwiched by the respective belts 34, 36, and 37 is transferred to the next step S13.

The respective belts 35 and 38 that move along the discarding path F2 move along different paths beginning at the rollers 41 and 42. Specifically, the respective outer support belts 35 return to the point (3) along a third return path R3 beginning at the roller 41. While, the respective separated portion sandwiching belts 38 return to the point (2) along the second return path R2 beginning at the roller 42. Thus, the separated portions 3b and 4b are released from the constraint by the respective belts 35 and 38. Then, the separated portions 3b and 4b are attracted by the discarding unit 18 that is provided in the vicinity of the respective rollers 41 and 42.

Meanwhile, as shown in FIG. 11, the respective support belts 34 and 35 are pressed to the peripheral surfaces of the support rollers 29 and 30 that are freely rotatable with respect to the driving shaft 26. Therefore, a conveying rate for conveying the partly-finished product 1Z with the respective support belts 34 and 35 and the rotating rate of the driving blades 27 (the driving shaft 26) may be individually set. Hereinafter, a description will be given of the controller 20 that controls the conveying rate and the rotating rate.

The controller 20 sets the conveying rate for conveying the partly-finished product 1Z with the conveying unit 19 and the rotating rate (angular rate) of the driving blades 27 based on a commanded value of the conveying rate input by the input unit 21 and outputs the conveying rate and the rotating rate to the cutting motor 33 and the conveying motor 39.

Here, the controller 20 sets the rotating rate of the driving blades at a rate faster than a target conveying rate based on the input from the input unit 21. Thus, the driving blades 27 move faster than the respective side panel pieces 3 and 4. Therefore, the respective side panel pieces 3 and 4 can be reliably cut off. The controller 20 according to the embodiment sets the rotating rate at an angular rate 1.5 to 2.0 times with respect to the target conveying rate.

As described above, both side portions in the width direction of the welded portions of the respective side panel pieces 3 and 4 are held when the respective side panel pieces 3 are welded to each other and the respective side panel pieces 4 are welded to each other. Therefore, the respective side panel pieces 3 and 4 can be prevented from moving at the welding.

Accordingly, the welding positions of the respective side panel pieces 3 and 4 can be accurately managed.

Further, the embodiment produces the following effects.

In step S12, the end portions of the side panel pieces 3 and 4 are cut off uniformly, thereby the appearance of the disposable diaper 1 can be enhanced.

Here, in the embodiment, in a state in which both side positions in the width direction of the region of the side panel pieces 3 and 4, the region including the welding target portions and the cutting target portions, are held, the side panel pieces 3 can be welded to each other while the side panel pieces 4 can be welded to each other and the respective side panel pieces 3 and 4 can be cut off. Thus, the respective side panel pieces 3 and 4 can also be prevented from moving when they are cut off. Therefore, the cutting positions as well as the welding positions can also be reliably managed as described above.

In addition, the separated portions 3b and 4b are conveyed along the discarding path F2 that is not used for the portions other than the separated portions 3b and 4b. Therefore, the separated portions 3b and 4b can be torn off from the other portions even in a state in which the separated portions 3b and 4b are imperfectly cut off (for example, a state in which the portions of the side panel pieces 3 and 4 across their cutting-plane line are joined to each other due to the tangling of fibers when the side panel pieces 3 and 4 are made of, for example, a nonwoven fabric).

Further, the separated portions 3b and 4b are released at the discarding unit 18 while being constrained between the respective outer support belts 35 and the respective separated portion sandwiching belts 38. In this way, it becomes possible to tear off the imperfectly cut-off separated portions 3b and 4b from the other portions and reliably discard the separated portions 3b and 4b at the discarding unit 18 as described above.

In addition, in the embodiment, the tentative fastening portions 3c and 4c are formed in step S10, i.e. the step between steps S9 and S11. Thus, at a stage before the respective side panel pieces 3 are welded to each other and the respective side panel pieces 4 are welded to each other after the diaper main body 2 of the partly-finished product 1Z is folded, the diaper main body 2 can be prevented from being unfolded by the tentative fastening portions 3c and 4c. Particularly, in the embodiment, the partly-finished product 1Z is held with respect to the inner support belt 34 by adsorption in the range between the point (1) and the point (2) in FIG. 7. Therefore, the diaper main body 2 can be effectively prevented from being unfolded in this range.

Note that although the embodiment describes the disposable diaper 1 in which the side panel pieces 3 and 4 are sandwiched between the inner sheet 10 and the outer sheet 11 as shown in FIG. 3, the disposable diaper 1 can also have a configuration in which the respective side panel pieces 3 and 4 are bonded on the inner sheet 10. In this case, it is necessary to reverse the order of steps S5 and S6 shown in FIG. 6.

Figure 6:
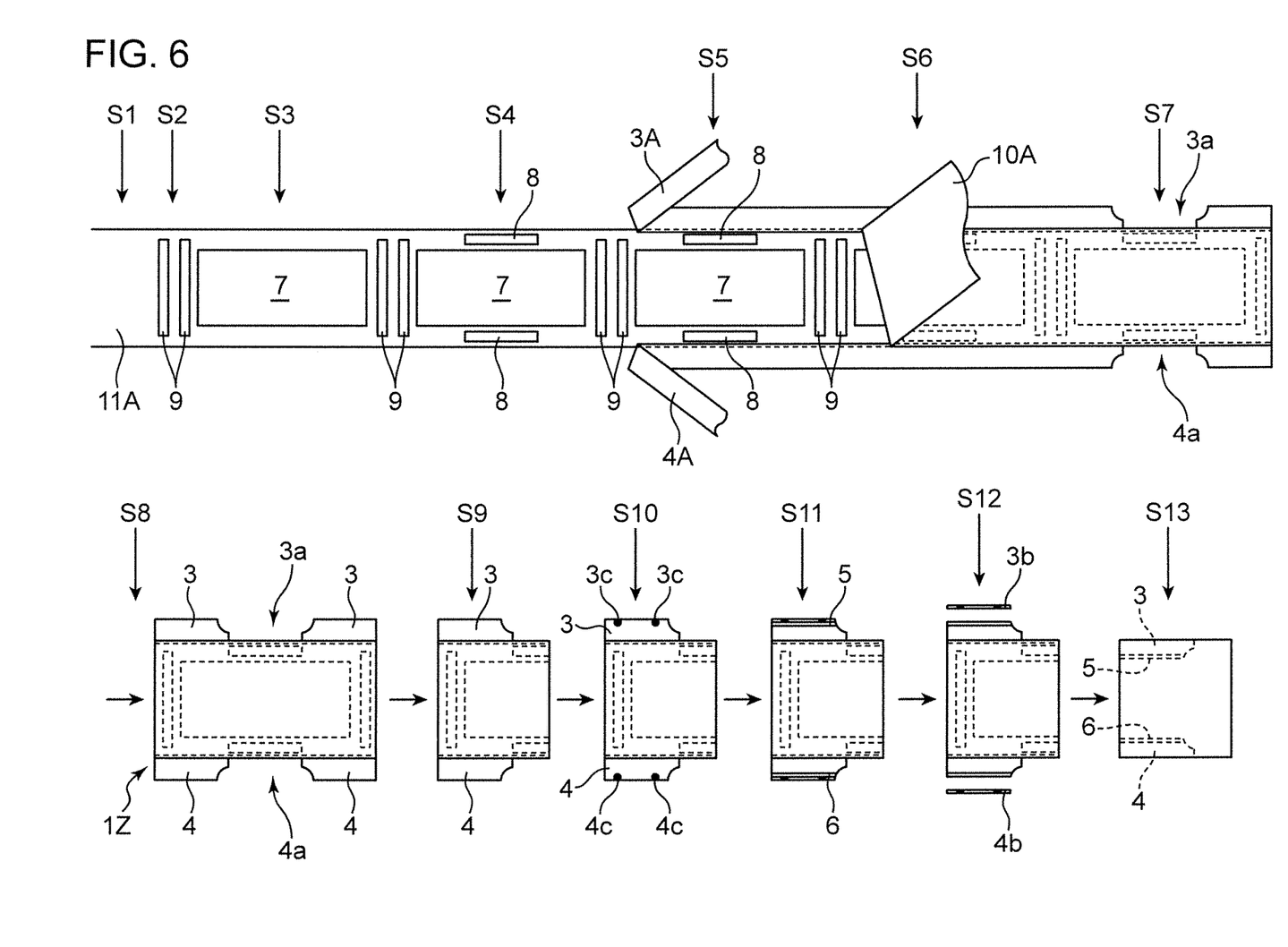
FIG. 6 is a process drawing showing a production method for the disposable diaper in FIG. 1.

In addition, although the embodiment exemplifies the method in which the side panel bands 3A and 4A are bonded to the outer sheet band 11A in step S5 and cut off in step S7 as shown in FIG. 6, the method of forming the side panel pieces 3 and 4 is not limited to this. For example, the side panel pieces 3 and 4 may be prepared in advance and bonded to the outer sheet band 11A at a pitch corresponding to the gap portions 3a and 4a in step S5. In this case, step S7 may be omitted.

Moreover, the respective elastic members 8 for legs and the respective elastic members 9 for waist may be bonded to the inner side of the inner sheet 10 and/or the outer side of the outer sheet.

Note that the specific embodiment described above mainly includes the inventions having the following configurations.

In order to solve the problem, the present invention provides a disposable diaper production method for producing a disposable diaper having a main body portion that extends from a front belly part to a back part via a crotch part and a pair of side portions that covers side surfaces of a lumbar part of a wearer when the disposable diaper is worn, the method comprising: a constituents producing step of producing constituents including the main body portion and four side pieces each of which protrudes from both ends of the main body portion in a longitudinal direction to both outer sides in a width direction of the main body portion; a folding step of folding the main body portion in the longitudinal direction to form two sets of two mutually-overlapping side pieces; a conveying step of conveying the folded constituents along the longitudinal direction; and a welding step of welding the mutually-overlapping side pieces to each other along a conveying direction for each set of the two side pieces of the constituents being conveyed to form the pair of side portions, wherein the conveying step conveys the constituents in a state in which both side portions in the width direction of a portion of the respective side pieces to be welded are held for each set of the two side pieces when the respective side pieces are welded to each other in the welding step.

In addition, the present invention provides a disposable diaper production device for producing a disposable diaper having a main body portion that extends from a front belly part to a back part via a crotch part and a pair of side portions that covers side surfaces of a lumbar part of a wearer when the disposable diaper is worn, the device comprising: a folding unit that folds the main body portion in a longitudinal direction to form two sets of two mutually-overlapping side pieces for constituents including the main body portion and four side pieces each of which protrudes from both ends of the main body portion in the longitudinal direction to both outer sides in a width direction of the main body portion; a conveying unit that conveys the folded constituents along the longitudinal direction; and a welding unit that welds the mutually-overlapping side pieces to each other along a conveying direction for each set of the two side pieces of the constituents being conveyed to form the pair of side portions, wherein the conveying unit conveys the constituents in a state in which both side portions in the width direction of a portion of the respective side pieces to be welded are held for each set of the two side pieces when the respective side pieces are welded to each other by the welding unit.

According to these inventions, both the side portions in the width direction of the portion of the respective side pieces to be welded are held when the respective side pieces are welded to each other. Therefore, the respective side pieces can be prevented from moving when the respective side pieces are welded to each other.

Thus, according to the respective inventions, the welding position of the respective side pieces can be accurately managed.

The production method preferably further comprises a cutting step of cutting off end portions of the two side pieces uniformly for each set of the two side pieces after the welding step, wherein the conveying step preferably conveys the constituents in a state in which both side portions in the width direction of a region of the constituent, the region including the portion to be welded in the welding step and a portion to be cut off in the cutting step, are held over a period between the welding step and the cutting step.

In addition, the production device preferably further comprises a cutting unit that cuts off end portions of the two side pieces uniformly for each set of the two side pieces welded by the welding unit, wherein the conveying unit preferably conveys the constituents in a state in which both side portions in the width direction of a region of the constituent, the region including the portion to be welded by the welding unit and a portion to be cut off by the cutting unit, are held over a range between the welding unit and the cutting unit.

According to these aspects, the end portions of the two side pieces are cut off uniformly. Therefore, the appearance of the disposable diaper can be enhanced.

Here, in the respective aspects, in a state in which both the side portions in the width direction of the region of the constituent, the region including the welding target portion and the cutting target portions, are held, the side pieces can be welded to each other and cut off. Thus, the respective side pieces can also be prevented from moving when they are cut off. Therefore, the cutting positions as well as the welding positions can also be reliably managed as described above.

The production method preferably further comprises a discarding step of discarding separated portions of the respective side pieces, separated in the cutting step, to a discarding unit, wherein the conveying step preferably conveys, after the cutting step, portions other than the separated portions of the constituents along a main path while conveying the separated portions to the discarding unit along a discarding path that branches off from the main path.

In addition, the disposable diaper production device preferably further comprises a discarding unit that discards separated portions of the respective side pieces separated by the cutting unit, wherein the conveying unit preferably conveys, on a downstream side of the cutting unit, portions other than the separated portions of the constituents along a main path while conveying the separated portions to the discarding unit along a discarding path that branches off from the main path.

According to these aspects, the separated portions are conveyed along the path (discharge path), which is not used for the portions other than the separated portions. Therefore, the separated portions can be torn off from the other portions even in a state in which the separated portions are imperfectly cut off from the other portions (for example, a state in which the portions of the side pieces across their cutting-plane line are joined to each other due to the tangling of fibers when the side pieces are made of, for example, a nonwoven fabric).

In the production method, the conveying step preferably conveys portions corresponding to the separated portions while sandwiching the portions corresponding to the separated portions with a pair of sandwiching members from both front and rear sides thereof over a period between the welding step and the discarding step and separates the pair of sandwiching members from each other at the discarding unit.

In addition, in the production device, the conveying unit preferably has a pair of sandwiching members, conveys portions corresponding to the separated portions while sandwiching the portions corresponding to the separated portions with the pair of sandwiching members from both front and rear sides thereof over a range between the welding unit and the discarding unit, and separates the pair of sandwiching members from each other at the discarding unit.

According to these aspects, the separated portions are released at the discarding unit while being constrained between the pair of sandwiching members. In this way, it becomes possible to tear off the imperfectly cut-off separated portions from the other portions and reliably discard the separated portions at the discarding unit as described above.

The production method preferably further comprises a tentative fastening step of tentatively fastening, before the welding step, the respective mutually-overlapping side pieces to each other at positions corresponding to the separated portions of the respective side pieces to be separated in the cutting step.

In addition, the production device preferably further comprises a tentative fastening unit that tentatively fastens, for the constituents before the respective side pieces are welded by the welding unit, the respective mutually-overlapping side pieces to each other at positions corresponding to the separated portions of the respective side pieces to be separated by the cutting unit.

According to these aspects, at a stage before the respective side pieces are welded to each other after the main body portion is folded, the main body portion can be prevented from being unfolded by the tentative fastening unit.

The invention claimed is:

1. A disposable diaper production method for producing a disposable diaper having a main body portion that extends from a front belly part to a back part via a crotch part and two side portions that cover side surfaces of a lumbar part of a wearer when the disposable diaper is worn, side seals being formed respectively on the two side portions, the method comprising:
    a constituents producing step of producing constituents including the main body portion and four side pieces each of which protrudes from both ends of the main body portion in a longitudinal direction to both outer sides in a width direction of the main body portion;
    a folding step of folding the main body portion in the longitudinal direction to form two sets of two mutually-overlapping side pieces;
    a conveying step of conveying the folded constituents along the longitudinal direction;
    a welding step of welding the mutually-overlapping side pieces to each other along a conveying direction for each set of the two side pieces of the constituents being conveyed to form the two side portions with the side seals;
    a cutting step of cutting off end portions of the two side pieces uniformly for each set of the two side pieces after the welding step; and
    a discarding step of discarding separated portions of the respective side pieces, separated in the cutting step, wherein
    the conveying step conveys the constituents in a state in which both outside portions in the width direction of portions of the side pieces on which the respective side seals are to be formed and both inside portions in the width direction of portions of the side pieces on which the respective side seals are to be formed are held for each set of the two side pieces when the respective side pieces are welded to each other in the welding step;
    the conveying step conveys the constituents in a state in which both side portions in the width direction of a region of the constituent, the region including the portion to be welded in the welding step and a portion to be cut off in the cutting step, are held over a period between the welding step and the cutting step; and the conveying step conveys, after the cutting step, portions other than the separated portions of the constituents along a main path while conveying the separated portions along a discarding path that branches off from the main path, and the disposable diaper production method further comprising:

providing a conveying unit that has:
- an inner support belt that supports a partly folded product of the disposable diaper between portions of the side pieces on which the respective side seals are to be formed,
- two outer support belts that support the side pieces on the outer sides of the respective portions of the side pieces on which the respective side seals are to be formed,
- two panel sandwiching belts that sandwich the side pieces between the panel sandwiching belts and the inner support belt, and
- two separated portion sandwiching belts that sandwich the side pieces between the separated portion sandwiching belt and the respective outer support belts, and wherein the conveying step conveys the constituents by being sandwiched between the panel sandwiching belts and the inner support belt and between the separated portion sandwiching belts and the outer support belts when the respective side pieces are welded to each other in the welding step.

2. The disposable diaper production method according to claim 1, further comprising:
a tentative fastening step of tentatively fastening, before the welding step, the respective mutually-overlapping side pieces to each other at positions corresponding to the separated portions of the respective side pieces to be separated in the cutting step.

3. The disposable diaper production method according to claim 1, wherein the conveying step separates the outer support belts and the separated portion sandwiching belts from each other at an end of the discarding path.

4. The disposable diaper production method according to claim 3, further comprising:
a tentative fastening step of tentatively fastening, before the welding step, the respective mutually-overlapping side pieces to each other at positions corresponding to the separated portions of the respective side pieces to be separated in the cutting step.

* * * * *